United States Patent
Mallet et al.

(10) Patent No.: US 6,723,315 B1
(45) Date of Patent: Apr. 20, 2004

(54) METHOD FOR TREATING AMYOTROPHIC LATERAL SCLEROSIS

(75) Inventors: Jacques Mallet, Paris (FR); Philippe Kennel, Issy les Moulineaux (FR); Frédéric Revah, Paris (FR); Axel Kahn, Paris (FR); Georg Haase, Paris (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/254,617

(22) PCT Filed: Sep. 10, 1997

(86) PCT No.: PCT/FR97/01589

§ 371 (c)(1),
(2), (4) Date: Mar. 22, 1999

(87) PCT Pub. No.: WO98/11213

PCT Pub. Date: Mar. 19, 1998

(30) Foreign Application Priority Data

Sep. 13, 1996 (FR) .............................. 96 11186

(51) Int. Cl.[7] .................. A01N 63/00; A01N 65/00; A61K 48/00; C12N 15/00; C12N 15/63
(52) U.S. Cl. .................. 424/93.2; 424/93.1; 424/93.6; 435/320.1
(58) Field of Search .............................. 424/93.1, 93.2, 424/93.6; 435/320.1; 514/44

(56) References Cited

U.S. PATENT DOCUMENTS 6,200,798 B1  3/2001  Yeh et al.
6,245,330 B1  6/2001  Horellou et al.

FOREIGN PATENT DOCUMENTS

| EP | 558 861 | 9/1993 |
|----|---------|--------|
| WO | WO 91/04316 | 4/1991 |
| WO | WO 94/08026 | 4/1994 |
| WO | WO 95/25804 | 9/1995 |
| WO | WO 95/26408 | 10/1995 |
| WO | WO 99/01175 | 1/1999 |

OTHER PUBLICATIONS

Friedmann; Overcoming the Obstacles. 1997, Scientific American: 96–101.*

Verma et. al.; Gene therapy– promises, problems and prospects, 1997, Nature vol. 389:239–242.*

Orkin et al.; Report and Recommendations of the Panel to Assess the NIH Investment in Research on Gnee Therapy, 1995.*

Haase et al., Gene Therapy of Murine Motor Neuron Disease Using Adenoviral Vectors For Neurotrophic Factors. Nature Medicine, 3(4), 429–436 (1997).

* cited by examiner

*Primary Examiner*—Anne-Marie Falk
(74) *Attorney, Agent, or Firm*—Wiley Rein & Fielding LLP

(57) ABSTRACT

The invention concerns a novel method for treating motor neuron diseases and particularly amyotrophic lateral sclerosis. It consists more particularly in the systemic administration of expression systems of neurotrophic factors.

65 Claims, 4 Drawing Sheets

METHOD FOR TREATING AMYOTROPHIC LATERAL SCLEROSIS

Figure 1:
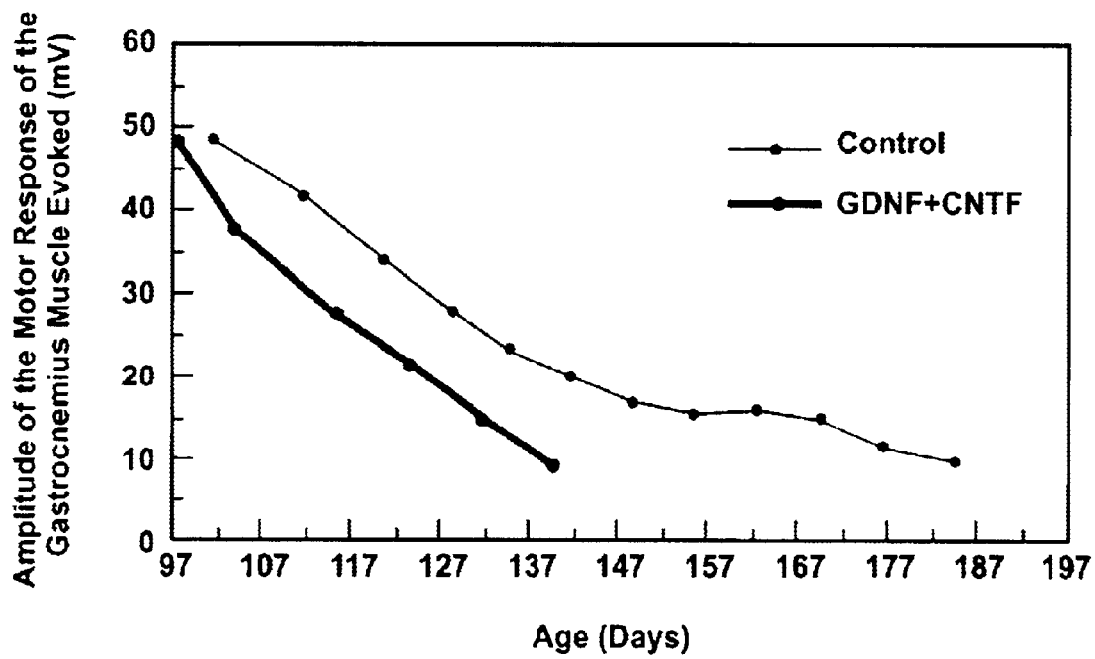

The present invention relates to a novel method for the treatment of motor neurone diseases and in particular of amyotrophic lateral sclerosis. It equally relates to vectors and pharmaceutical compositions allowing the prolonged expression of therapeutic factors, utilizable for the treatment of ALS. More precisely, the present invention relates to the treatment of ALS by systemic administration of therapeutic genes.

Amyotrophic lateral sclerosis (ALS), also known under the name of Charcot's disease and Lou Gehrig's disease was described for the first time by Charcot in 1865. ALS is a fatal disease resulting from the degeneration of motor neurones and corticospinal tracts. With an incidence at present of 2.5/100,000 and, constantly on the increase, a prevalence of 6–10/100,000, ALS affects 90,000 people in the developed countries, for the most part adults who are still young (between 50 and 60). The disease is accompanied by progressive paralysis, leading to the total loss of motor and respiratory functions and then to death with a delay of two to eight years after the appearance of the first symptoms (three years on average).

5% of the cases of ALS are of familial origin and 95% of the cases are sporadic. The physio-pathological origin of the sporadic forms of ALS remains unknown. Several hypotheses have been proposed. The motor neurons degeneration could result from an alteration in the metabolism of glutamate leading to an increase in the concentration of this exciter amino acid in the motor cortex and the spinal cord ("excitotoxic" hypothesis, review in Rothstein, 1995). The possibility of an autoinmune component has likewise been put forward on the basis of the presence of auto-antibody against the voltage-sensitive calcium channels in certain patients (review in Appel et al., 1995). The implication of environmental factors such as exposure to certain viruses (review in Gastaut, 1995), or to aluminium (Yase, 1984) is likewise possible.

The studies bearing on the hereditary forms of ALS have allowed it to be shown that point mutations in the gene for cupro-zinc containing superoxide dismutase, localized on the 21q22-1 chromosome, are responsible for the pathology in 20% of the familial forms (Rosen et al., 1993, review in Rowland, 1995). These mutations do not cause reduction of the dismutase activity of the SOD (review in Rowland, 1995). The mutated enzymes produce potentially cytotoxic hydroxyl radicals which are not produced by the wild-type SOD (Yim et al., 1996). The detailed study of the functional effect of the mutations on the enzymatic activity of the SOD and on the cellular viability in the end ought to allow the physiopathology of the familial forms of ALS to be understood, and, by extension, light to be thrown on the physiopathology of all of the forms of ALS.

Work bearing on factors capable of influencing the survival of the motor neurones has allowed a potential neuroprotector role of several neurotrophic factors to be demonstrated (review in Windebank, 1995; Henderson, 1995). Thus, motor neurone protection effects in vitro have been observed especially with BDNF (Oppenhoem et al., 1992, Yan et al., 1992 Sendtner et al., 1992, Henderson et al., 1993, Vejsada et al., 1995), NT-3 (Henderson et al., 1993), GDNF (Henderson et al., 1994, Oppenheim et al., 1995), three cytokines, CNTP, LIF (review in Henderson, 1995) and cardiotrophin-1 (Pennica at al., 1996), with IGF-1 (Lewis et al., 1993) and members of the FGF family (Hughes et al., 1993). All of these data suggest that the neurotrophic factors mentioned increase the survival of motor neurones under various experimental conditions. However, the use of neurotrophic factors in animal models of ALS or in human clinical trials as yet have not given convincing results. This use has never demonstrated any therapeutic effect and is always accompanied by undesirable secondary effects such as loss of weight, inflammation, fever, etc., which limit interest in trophic factors in the treatment of ALS and have led to the premature interruption of the first ALS-CNTF clinical trials by Regeneron (systemic administration) (Barinaga et al., 1994). It has thus not been possible as yet either to confirm interest in neurotrophic factors for the treatment of ALS, or to exploit their properties for a possible therapeutic approach.

On account of this, at the present time there is no means allowing ALS to be cured and very few medicaments having a therapeutic effect. Rilute® is the only treatment available today. The administration of riluzole (Rilutek®) allows the progression of the disease to be slowed, but no therapeutic effect has been demonstrated on the motor function. In addition, clinical trials based on the administration of CNTF have been interrupted prematurely for lack of results (Barinaga et al., 1994). Thus today there exists a real and important need to have available a method allowing motor neurone disorders to be treated, and in particular ALS.

The object of the present invention is especially to propose a novel approach for the treatment of the pathologies of motor neurones, such as ALS, based on gene therapy. More particularly, the present invention describes vector systems allowing the survival of motor neurones involved in these pathologies to be promoted directly, by the efficient and prolonged expression of certain trophic factors.

A first aspect of the invention relates to a method of treatment of ALS comprising the systemic administration of a nucleic acid coding for a neurotrophic factor. Another aspect of the invention relates to the use of a nucleic acid coding for a neurotrophic factor for the preparation of a pharmaceutical composition intended for the treatment of ALS. Another aspect of the invention resides in the construction of particular vectors allowing the expression of therapeutically effective quantities, in relation to ALS, of trophic factors. Another aspect of the invention relates to the administration of expression systems allowing the production of one or more trophic factors, as well as pharmaceutical compositions comprising the said expression systems. It likewise relates to the creation of novel vectors allowing the co-expression of trophic factors in vivo.

The present invention thus more precisely relates to a novel method of treatment of ALS based on the continuous in vivo expression of trophic factors.

The present invention now shows that it is possible in vivo to obtain a particularly pronounced therapeutic effect by in vivo production of nourotrophic factors. The applicant has especially shown that the in vivo injection of neurotrophic factor expression systems, by the systemic routs, allows a continuous production of therapeutic factors to be obtained, and that this production was sufficient to obtain a therapeutic benefit in the motor neurone pathologies, in particular ALS. Thus, the applicant has shown that the systemic administration of these expression systems leads to a very significant increase in the duration of life, accompanied by an improvement in the motor response evoked, as determined by electromyography. The results described demonstrate that this administration route allows an appropriate bioavailability of neurotrophic factors to be obtained, without toxicity effects. This therapeutic approach thus allows therapeutically active quantities of molecules to be produced, while remaining below the threshold of toxicity of these molecules. Thus, even though a protein of the size of a neurotrophic factor, administered in a systemic manner, only penetrates the nervous system with a low efficacy because of the blood-brain barrier, the method of the invention unexpectedly allows a significant therapeutic effect to be obtained. In addition, the method of the invention allows doses of therapeutic factors to be used which are below the toxicity threshold and do not induce secondary effects.

A first object of the invention thus resides in a method of treatment of ALS comprising the administration, by the systemic route, of an expression system of a neurotrophic factor. Another object of the invention likewise resides in the use of an expression system of a neurotrophic factor for the preparation of a pharmaceutical composition intended for the treatment of ALS, by administration systemically. The invention likewise relates to a method to prolong the duration of life of mammals suffering from ALS, comprising the administration by the systemic route of an expression system of a neurotrophic factor.

In the sense of the invention, the term "expression system" designates any construct allowing the in vivo expression of a nucleic acid coding for a neurotrophic factor. Advantageously, the expression system comprises a nucleic acid coding for a neurotrophic factor under the control of a transcriptional promoter (expression cassette). This nucleic acid can be a DNA or an RNA. Concerning a DNA, it is possible to use a cDNA, a gDNA or a hybrid DNA, that is to say a DNA containing one or more introns of the gDNA, but not all. The DNA can likewise be a synthetic or semi-synthetic DNA, and in particular a DNA synthesized artificially to optimize the codons or create reduced forms.

The transcriptional promoter can be any functional promoter in a mammalian cell, preferably human. It can be the promoter region naturally responsible for the expression of the neurotrophic factor considered when this is capable of functioning in the cell or organism concerned. It can likewise be regions of different origin (responsible for the expression of other proteins, or even synthetic). Especially, it can be promoter regions of eucaryotic or viral genes. For example, it can be promoter regions from the genome of the target cell. Among the eucaryotic promoters, it is possible to use any promoter or derived sequence stimulating or suppressing the transcription of a gene in a manner which is specific or non-specific, inducible or non-inducible, strong or weak. It can in particular be ubiquitous promoters (promoter of the HPRT, PGK, α-actine, tubulin genes, etc.), promoters of the intermediate filaments (promoter of the GFAP, desmin, vimentin, neurofilaments, keratin genes, etc.), promoters of therapeutic genes (for example the promoter of the MDR, CFTR, Factor VIII, ApoAX genes, etc.), specific tissue promoters (promoter of the pyruvate kinase, villin, fatty acid-bound intestinal protein, smooth muscle α-actin gene, etc.) or even of promoters responding to a stimulus (steroid hormone receptor, retinoic acid receptor, etc.). In the same way, it can be promoter sequences from the genome of a virus, such as, for example, the promoters of the E1A and adenovirus MLP genes, the early promoter of CMV, or even the promoter of LTR of RSV, etc. In addition, these promoter regions can be modified by addition of activation sequences, regulation sequences or sequences allowing a tissue-specific or majority expression.

Within the context of the invention, a constitutive eucaryotic or viral promoter is advantageously used. It is more particularly a promoter chosen from among the promoter of the KPRT, PGK, α-actin, tubulin genes or the promoter of the E1A and adenovirus MLP genes, the early promoter of CMV, or even the promoter of LTR of RSV.

In addition, the expression cassette advantageously contains a signal sequence directing the product synthesized in the secretion tracts of the target cell. This signal sequence can be the natural signal sequence of the product synthesized, but it can likewise be any other functional signal sequence, or an artificial signal sequence.

Finally, the expression cassette generally comprises a region situated in 3', which specifies a transcription end signal and a polyadenylation site.

The trophic factors used in the context of the invention are essentially classed under three families: the nourotrophin family, the neurokine family and the TGF beta family (for review, see Henderson, Adv. Neurol. 68 (1995) 235).

More preferentially, in the neurotrophin family, it is preferred in the context of the invention to use BDNF, NT-3 or NT-4/5.

The neurotrophic factor derived from the brain (BDNF), described by Thoenen (Trends in NeuroSci. 14 (1991) 165), is a protein of 118 amino acids and of molecular weight 13.5 kD. In vitro, BDNF stimulates the formation of neurites and the survival in culture of ganglionic neurones of the retina, cholinergic neurones of the septum as well as dopaminergic neurones of the mesencephalon (review by Lindsay in Neurotrophic Factors, Ed, (1993) 257, Academic Press). The DNA sequence coding for human BDNF and for rat BDNF has been cloned and sequenced (Maisonpierre et al., Genomics 10 (1991) 558), as well as especially the sequence coding for porcine BDNF (Leibrock et al., Nature 341 (1989) 149). Though its properties would be potentially interesting, the therapeutic administration of BDNF is running into various obstacles. In particular, the lack of bioavailability of BDNF limits any therapeutic use. The brain-derived neurotrophic factor (BDNF) produced in the context of the present invention can be human BDNF or animal BDNF.

Neurotrophin 3 (NT3) is a secreted protein of 119 aa which allows the in vitro survival of neurones even at very low concentrations (Henderson et al., Nature 363, 266–270 (1993)). The sequence of the cDNA coding for human NT3 has been described (Hohn et al., Nature 344 (1990) 339).

The TGF-B family especially comprises the glial cell-derived neurotrophic factor. The glial cell-derived neurotrophic factor, GDNF (L.-F. Lin et al., Science, 260, 1130–1132 (1993)) is a protein of 134 amino acids and of molecular weight 16 kD. It has the essential capacity in vitro of promoting the survival of dopamineric neurones and of motor neurones (review in Henderson, 1995). The glial cell-derived neurotrophic factor (GDNF) produced in the context of the present invention can be human GDNF or animal GDNF. The CDNA sequences coding for human GDNF or rat GDNF have been cloned and sequenced (L.-F. Lin, D. Doherty, J. Lile, S. Besktesh, F. Collins, Science, 260, 1130–1132 (1993)).

Another neurotrophic factor which can be used in the context of the present invention is especially CNTP ("Ciliary NeuroTrophic Factor"). CNTF is a neurokine capable of preventing the death of neurones. As indicated above, clinical trials have been interrupted prematurely for lack of results. The invention now allows the prolonged and continuous in vivo production of CNTF, on its own or in combination with other trophic factors, for the treatment of ALS. cDNA and the human and murine CNTF gene have been cloned and sequenced (EP385 060; WO91/04316).

Other neurotrophic factors which can be used in the context of the present invention are, for example, IGF-1 (Lewis et al., 1993) and fibroblast growth factors (FGFa, FGFb). In particular, IGF-I and FGFa are very interesting candidates. The sequence of the gene of FGFa has been described in the literature, as well as vectors allowing its expression in vivo (WO95/25803).

The genes coding for BDNF, GDNF, CNTF and NT3 are all particularly interesting for the implementation of the present invention.

According to a first mode of realization, the expression system of the invention allows the production of a single neurotrophic factor in vivo. In this case, the expression system only contains an expression cassette. Preferentially, the expression system of the invention allows the in vivo production of a neurotrophic factor chosen from among neurotrophins, neurokines and TGFs. It is more preferentially a factor chosen from among BDNF, GDNF, CNTF, NT3,FGFa and IGF-I.

According to another mode of realization, the expression system of the invention allows the production of two neurotrophic factors in vivo. In this mode of realization, the expression system contains either two expression cassettes or a single cassette allowing the simultaneous expression of two nucleic acids (bicistronic unit). When the system comprises two expression cassettes, these can use identical or different promoters.

Preferentially, the expression system of the invention allows the in vivo production of combinations of the following neurotrophic factors: BDNF and GDNF; BDNF and NT3; GDNF and NT3, CNTF and BDNF, CNTF and MT3, CNTF and GDNF.

Advantageously, the Applicant has in fact shown that the administration of 2 neurotrophic factor expression systems is manifested by a significant therapeutic effect. In the expression systems of 2 neurotrophic factors, promoters of identical or similar strength are used, and an identical or similar number of copies of nucleic acids. Generally, the respective quantity of the two factors produced in vivo is sufficiently close. However, it may be preferable in certain situations to produce different quantities of each factor. In this case, it is possible to use either promoters of different strength, or a system in which numbers of copies of different genes are present, or to vary the doses administered.

In the expression systems of the invention, the expression cassette (s) is (are) advantageously part of a vector. In particular, it can be a viral or plasmid vector. In the case of an expression system containing several expression cassettes, the cassettes can be carried by separate vectors, or by the same vector.

The vector used can be a standard plasmid vector, containing, in addition to the expression cassette(s) according to the invention, a replication origin and a marker gene. Different types of improved vectors have moreover been described, being devoid of marker gene and of replication origin (PCT/FR96/00274) or possessing, for example, a conditional replication origin (FR95 10825). These vectors can be used advantageously in the context of the present invention.

The vector used can likewise be a viral vector. Different vectors have been constructed starting from a virus having remarkable gene-transfer properties. It is possible to mention, more particularly, adenoviruses, retroviruses, AAVs and herpes virus. For their use as gene-transfer vectors, the genome of these viruses is modified so as to render them incapable of autonomous replication in a cell. These viruses are called defective for replication. Generally, the genome is modified by substitution of the essential trans regions in viral replication by the expression cassette(s).

In the context of the invention, it is preferred to use a viral vector derived from the adenoviruses. Adenoviruses are linear double-stranded DNA viruses of a size of approximately 36 (kilobases) kb. Their genome especially comprises a repeated inverted sequence (ITR) at each end, an encapsidation sequence (Psi), early genes and late genes. The principal early genes are contained in the E1, E2, E3 and E4 regions. Among these, the genes contained in the E1 region especially are necessary for viral propagation. The principal late genes are contained in the L1 to L5 regions. The genome of the Ad5 adenovirus has been entirely sequenced and is accessible in databases (see especially Genebank M73260). In the same way, parts, or even the whole of other adenoviral genomes (Ad2, Ad7, Ad12, etc.) have likewise been sequenced.

For their use as gene-transfer vectors, various constructs derived from adenoviruses have been prepared, incorporating various therapeutic genes. More particularly, the constructs described in the prior art are adenoviruses from which the E1 region has been deleted and which are essential for viral replication, at the level of which are inserted heterologous DNA sequences (Levrero et al., Gene 101 (1991) 195; Gosh-Choudhury et al., Gene 50 (1986) 161). Moreover, to improve the properties of the vector, it has been proposed to create other deletions or modifications in the genome of the adenovirus. Thus, a heat-sensitive point mutation has been introduced into the mutant ts125, allowing the 72 kDa DNA linkage protein (DBP) to be inactivated (Van der Vliet et al., 1975). Other vectors comprise a deletion of another region essential to viral replication and/or propagation, the E4 region. The E4 region is in fact involved in the regulation of the expression of late genes, in the stability of late nuclear RNA, in the suppression of the expression of proteins of the host cell and in the efficacy of the replication of viral DNA. Adenoviral vectors in which the E1 and E4 regions are deleted thus have a transcription background noise and a very reduced expression of viral genes. Such vectors have been described, not example, in the Applications WO94/28152, WO95/02697, WO96/22378. In addition, vectors carrying a modification at the level of the IVa2 gene have likewise been described (WO96/10088).

The recombinant adenoviruses described in the literature are produced starting from various adenovirus serotypes. In fact, various adenovirus serotypes exist whose structure and properties vary somewhat, but which have a comparable genetic organization. More particularly, the recombinant adenoviruses can be of human or animal origin. Concerning the adenoviruses of human origin, it is preferentially possible to mention those classes in group C, in particular the adenoviruses of type 2 (Ad2), 5 (Ad5), 7 (Ad7) or 12 (Ad12). Among the different adenoviruses of animal origin, it is possible to preferentially mention the adenoviruses of canine origin, and especially all the strains of the CAV2 adenoviruses [Manhattan or A26/61 (ATCC VR-800) strain, for examples]. Other adenoviruses of animal origin are especially mentioned in the Application WO94/26914 incorporated by reference in the present application.

In a preferred mode of implementation of the invention, the recombinant adenovirus is a human adenovirus of group C. More preferentially, it is an Ad2 or Ad5 adenovirus.

The recombinant adenoviruses are produced in an encapsidation line, that is a line of cells capable of transcomplementing one or more of the deficient functions in the recombinant adenoviral genome. One of these lines is, for example, the 293 line into which a part of the genome of the adenovirus has been integrated. More precisely, the 293 line is a line of renal human embryonic cells containing the left end (approximately 11–12%) of the genome of the serotype 5 adenovirus (Ad5), comprising the left ITR, the encapsidation region, the E1 region, including E1a and E1b, the region coding for the PIX protein and a part of the region coding for the pIVa2 protein. This line is capable of trans-complementing defective recombinant adenoviruses for the E1 region, that is devoid of any or part of the E1 region, and of producing viral stocks having very high titres. This line is likewise capable of producing, at a permissive temperature (32° C.), stocks of virus containing in addition the heat-sensitive E2 mutation. Other cell lines capable of complementing the E1 region have been described, based especially on A549 human lung carcinoma cells (WO94/28152) or on human retinoblasts (Hum. Gen. Ther. (1996) 215). Moreover, lines capable of trans-complementing several functions of the adenovirus have likewise been described. In particular, it is possible to mention lines complementing the E1 and E4 regions (Yeh et al., J. Virol. 70 (1996) 559; Cancer Gen. Ther. 2 (1995) 322; Krougliak et al., Hum. Gen. Ther. 6 (1995) 1575) and lines complementing the E1 and E2 regions (WO94/28152, WO95/02697, WO95/27071). The recombinant adenoviruses are usually produced by introduction of the viral DNA into the encapsidation line, followed by lysis of the cells after approximately 2 or 3 days (the kinetics of the adenoviral cycle being from 24 to 36 hours). After the lysis of the cells, the recombinant viral particles are isolated by centrifugation in a caesium chloride gradient. Alternative methods have been described in the Application FR96 0164 incorporated by reference in the present application.

The expression cassette of the therapeutic gene(s) can be inserted into various sites of the genome of the recombinant adenovirus according to the techniques described in the prior art. It can first of all be inserted at the level of the E1 deletion. It can likewise be inserted at the level of the E3 region, in addition or in substitution of sequences. It can likewise be localized at the level of the deleted E4 region. For the construction of vectors carrying two expression cassettes, one can be inserted at the level of the E1 region, the other at the level of the E3 or E4 region. The two cassettes can likewise be introduced at the level of the same region.

As indicated above, in the case of expression systems containing several expression cassettes, the cassettes can be carried by separate vectors, or by the same vector. The present invention is more specifically aimed at the perfecting of vectors which are particularly efficacious at delivering in vivo and in a localized manner therapeutically active quantities of GDNF, of BDNF, of NT3 and of CNTF. More precisely, the present invention relates to the systemic injection of an expression system comprising two gene-transfer vectors each carrying a gene coding for a neurotrophic factor. The invention likewise relates to the systemic injection of an expression system comprising a bicistronic vector allowing the coexpression of the two genes. Preferentially, the present invention relates to the systemic injection of an expression system comprising two vectors, one carrying the gene coding for CNTF and the other the gene coding for NT3, or one the gene coding for CNTF and the other the gene coding for BDNF, or one the gene coding for GDNF and the other the gene coding for NT3.

More preferably, the transfer vectors used are adenoviral vectors. The Applicant has in fact shown the efficacy of the use of adenovirus coding for neurotrophic factors injected by the i.v. route in the treatment of different animal models of ALS. In particular, the results presented in the examples show, for the first time in an animal model of a familial form of ALS, $FALS_{G93A}$ mice, a significant increase in the duration of life, accompanied by better electromyographic performances. The only treatment today proposed for patients suffering from ALS is riluzole (Rilutek®) which increases by several months the hope of survival of the sufferers. It has likewise been demonstrated that riluzole administered to $FALS_{G93A}$ mice is able to increase by 13 days their average duration of live (Gurney et al., 1996). It can thus be predicted that any treatment increasing by more than 13 days the duration of life of $FALS_{G93A}$ mice is capable of providing to the patients a therapeutic benefit which is superior to that of riluzole. The results presented in the examples show that the therapeutic approach according to the invention allows the average duration of life of $FALS_{G93A}$ mice to be increased by approximately 30 days. This constitutes a very significant improvement in the duration of life, and represents the first demonstration of a therapeutic benefit of this importance on models of ALS.

The pmn mice constitute another model of ALS, characterized by an earlier and more rapid degeneration of the motor neurones and by an average length of life of approximately 40 days. The results presented in the examples show that the therapeutic approach according to the invention allows the average length of life of the pmn mice to be prolonged to 40 to 53 days, which is a significant improvement of more than 30%. This prolongation of the treated pmu mice is also accompanied by a significant reduction of their motor neurone degeneration.

All of the results obtained by this novel therapeutic approach show for the first time a significant improvement of different clinical, electromyographic and histological parameters, in two different models of ALS.

According to the invention, the production in vivo of trophic factors is obtained by systemic administration. The results presented in the examples show that this mode of administration allows a regular and continuous production of a trophic factor by the body of the patient himself to be obtained, and that this production is sufficient to generate a significant therapeutic effect. Systemic administration is preferentially an intravenous or intra-arterial injection. Intravenous injection is particularly preferred. This mode of injection is likewise advantageous in terms of tolerance and of ease of access. It additionally allows greater volumes to be injected than intramuscular injection, and in a repeated manner.

The present invention likewise relates to any pharmaceutical composition comprising an expression system of two neurotrophic factors. The pharmaceutical compositions of the invention advantageously contain pharmaceutically acceptable vehicles for an injectable formulation. In particular, they can be sterile, isotonic saline solutions (monosodium or disodium phosphate, sodium, potassium, calcium or magnesium chloride, etc., or mixtures of such salts), or dry compositions, especially lyophilized compositions, which, by addition, as the case may be, of sterilized water or physiological serum, allow the formation of injectable solutions. Other excipients can be used, such as, for example, stabilizer proteins (especially human serum albumin: FR96 03074) or a hydrogel. This hydrogel can be prepared starting from any biocompatible and non-cytotoxic polymer (homo or hetero). Such polymers have been described, for example, in the Application WO93/08845. Some of these, such as especially those obtained starting from ethylene oxide and/or propylene oxide are commercially available. In addition, when the expression system is composed of plasmid vectors, it can be advantageous to add to the pharmaceutical compositions of the invention chemical or biochemical agents favouring the transfer of genes. In this respect, it is possible more particularly to mention cationic polymers of the polylysine type, $(LKLK)_n$, (LKKL)$_n$ such as described in the Application WO95/21931, polyethylene imine (WO96/02655) and DEAE-dextran or even cationic or lipofectant lipids. They have the property of condensing DNA and of promoting its association with the cell membrane. Among the latter, it is possible to mention lipopolyamines (lipofectamine, transfectam, such as described in the Application WO95/18863 or WO96/17823) various cationic or neutral lipids (DOTMA, DOGS, DOPE, etc.) as well as peptides of nuclear origin (WO96/25508), possibly functionalized to target certain tissues. The preparation of a composition according to the invention using such a chemical vector is carried out according to any technique known to the person skilled in the art, generally by simple contacting of the different components.

The doses of expression system administered depend on several factors, and especially on the vector used, on the neurotrophic factor(s) involved, on the type of promoter used, on the stage of the pathology or even on the duration of the treatment studied. Generally, the expression system is administered in the form of doses comprising from 0.1 to 500 mg of DNA per kilogram, preferably from 1 to 100 mg of DNA per kilogram. Doses of 10 mg of DNA/kg approximately are generally used.

Being recombinant adenoviruses, they are advantageously formulated and administered in the form of doses of between $10^4$ and $10^{14}$ pfu, and preferably $10^6$ to $10^{10}$ pfu. The term pfu ("plaque forming unit") corresponds to the infectious power of an adenovirus solution, and is determined by infection of an appropriate cell culture, and is a measure, generally after 15 days, of the number of infected cell areas. The techniques of determination of the pfu titre of a viral solution are well documented in the literature.

Injection can be carried out by means of various devices, and in particular by means of syringes or by perfusion. Injection by means of syringes is preferred. In addition, repeated injections can be performed to increase still further the therapeutic effect.

According to a variant of the invention, this treatment can likewise be applied in combination with riluzole. The invention thus relates to a pharmaceutical composition comprising an expression system according to the invention and a pharmacologically effective quantity of riluzole, with a view to simultaneous administration or administration at intervals of time.

The results presented below illustrate the present invention without otherwise limiting its context. They demonstrate the particularly advantageous properties of the method of the invention which constitutes, to our knowledge, the first demonstration on an animal model of such a therapeutic benefit for ALS.

KEY TO FIGURES

FIG. 1: Comparison of the electromyographic performances of FALS$_{G93A}$ mice with or without administration of a CNTF-GDNF combination expression system.

Figure 2:
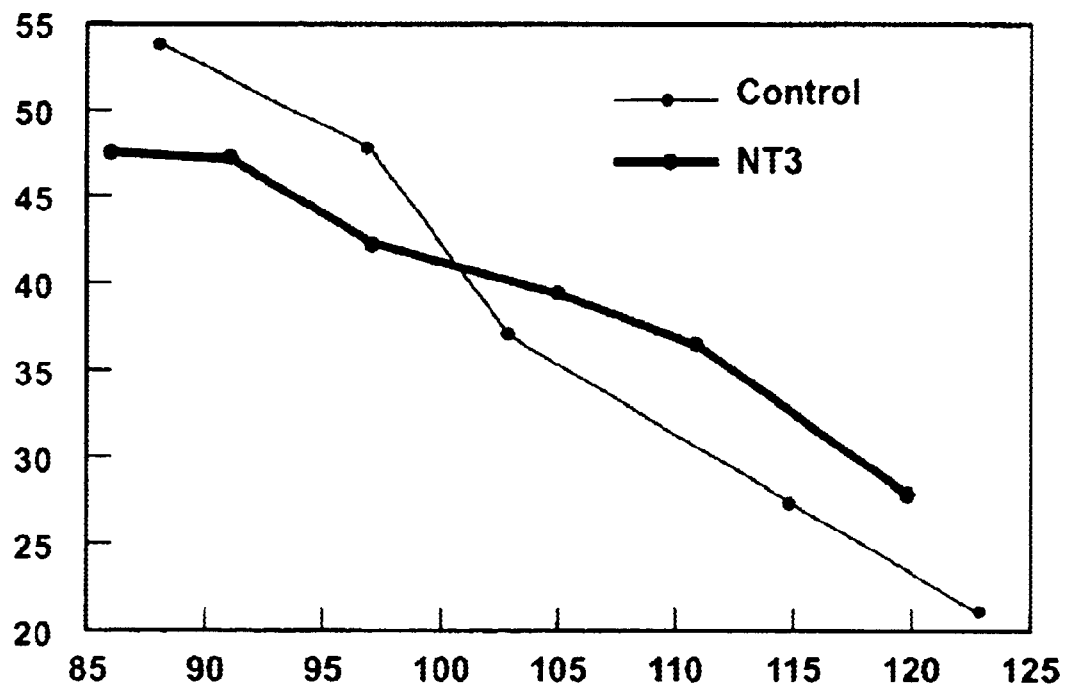

FIG. 2: Comparison of the electromyographic performances of FALS$_{G93A}$ mice with or without administration of an NT3 expression system.

Figure 3:
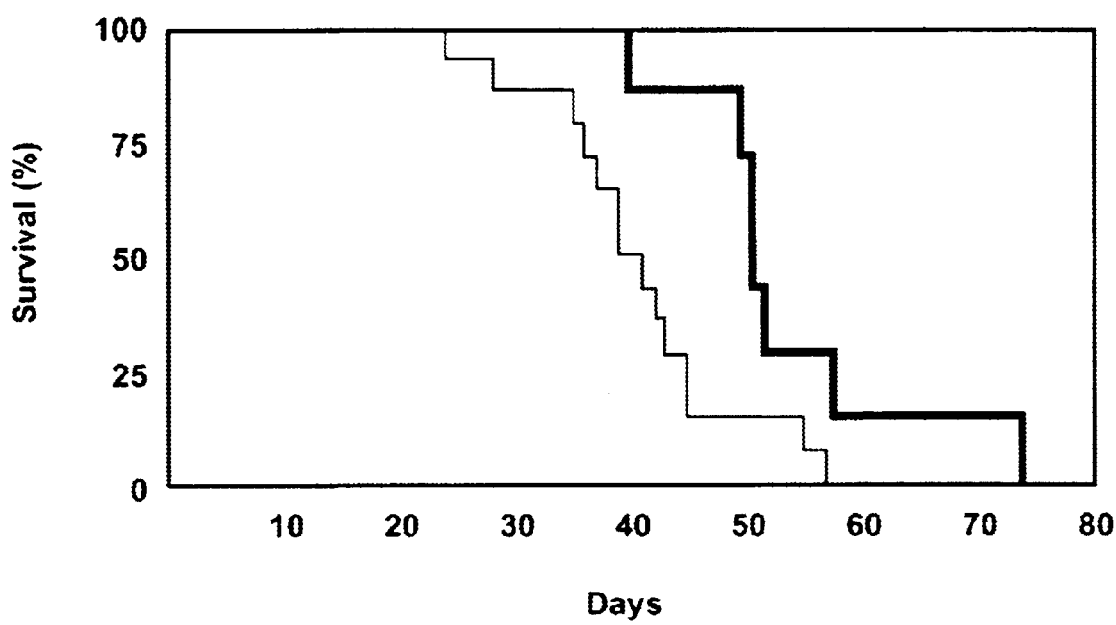

FIG. 3: Comparison of the survival of pmn mice with or without administration of a CNTF expression system. The survival of the pmn mice (in days) is expressed as a percentage of the animals analysed. pmn mice treated by administration of a CNTF expression system: 100%, n=7 (bold curve); non-treated pmn mice 100%, n=14 (normal line curve).

Figure 4:
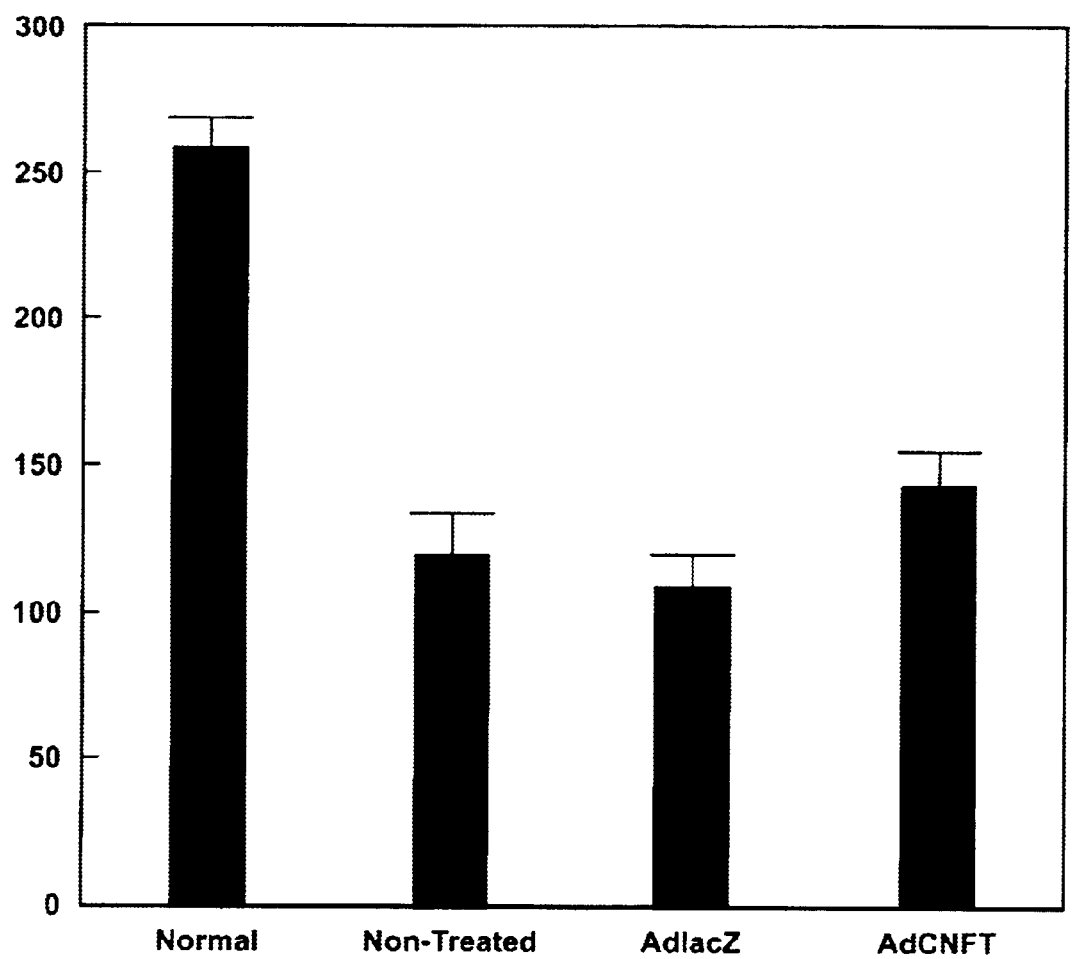

FIG. 4: Comparison of the motor neurone degeneration in pmn mice with or without administration of a CNTF expression system, the number of myelinized fibres in the phrenic nerve of mice is examined at an age of 25 days. Results: pmn mice with CNTF expression system (145, n=10); "non-treated" pmn mice without CNTF expression system (122, n=8); pmn mice treated with AdlacZ (111, n=8); "normal" Xt mice (263, n=4). The vertical bars represent the standard error of the mean (SEM).

EXAMPLES

1. Material and Methods

All of the experiments described below (construction of adenovirus, injection into mice, functional measurements) were carried out in an L3 confinement laboratory.

1—Animals

Several lines of transgenic mice expressing mutated forms of SOD responsible for the familial forms of ALS have been constructed to attempt to obtain a murine model of the pathology. Transgenic mice overexpressing mutated human SOD carrying a substitution of glycine 93 by alanine (FALS$_{G93A}$ mice) have a progressive motor neurone degeneration expressing itself by a paralysis of the limbs, and die at the age of 4–6 months (Gurney et al., 1994). The first clinical signs consist of a trembling of the limbs at approximately 90 days, then a reduction in the length of the step at 125 days (Chiu et al., 1995). At the histological level, vacuoles of mitochondrial origin can be observed in the motor neurones from approximately 37 days, and a motor neurons loss can be observed from 90 days (Chiu et al., 1995). Attacks on the myelinated axons are observed principally in the ventral marrow and a little in the dorsal region. Compensatory collateral reinnervation phenomena are observed at the level of the motor plaques (Chiu et al., 1995).

For Examples 2 to 10, we have chosen to use FALS$_{G93A}$ mice.

FALS$_{G93A}$ mice constitute a very good animal model for the study of the physiopathological mechanisms of ALS as well as for the development of therapeutic strategies. They in fact share with the familial forms of ALS a common physiopathological origin (SOD mutation), and a large number of histopathological and electromyographic characteristics.

Thus, we have characterized in the laboratory the electromyographic performances of the FALS$_{G93A}$ mice and shown that the FALS$_{G93A}$ mice fulfil the criteria of Lambert for ALS (Kennel et al., 1996): (1) reduction in the number of motor units with a concomitant collateral reinnervation; (2) presence of spontaneous denervation activity (fibrillations) and of fasciculation in the hind and fore limbs; (3) modification of the speed of motor conduction correlated with a reduction in the motor response evoked; (4) no sensory attack. Moreover we have shown that the facial nerve attacks were rare, even in the aged FALS$_{G93A}$ mice, which is also the case in the patients.

The FALS$_{G93A}$ mice come from Transgenic Alliance (L'Arbresle, France). Pregnant females are delivered each weeks. They give birth in the laboratory animal house. The immature mouse heterozygotes developing the disease are identified by PCR after taking a piece of tail and DNA extraction.

Other animal models having motor neurons degeneration exist (Sillevis-Smitt & De Jong, 1989; Price et al., 1994), either following an acute neurotoxic lesion (treatment with IDPN, with excitotoxins) or due to a genetic fault (wobbler, pmn, Mnd mice, HCSMA Dog). Among the genetic models, the pmn mice are particularly well characterized on the clinical, histological (schmalbruch 1991) and electromyographic (Kennel, 1996) level. The pmn mutation is transmitted in the autosomal recessive mode and has been localized on chromosome 13. The homozygous pmn mice develop a muscular atrophy and paralysis which is manifested in the rear members from the age of two to three weeks and which then generalistes. All the non-treated pmn mice die before six to seven weeks of age. The degeneration of their motor neurones begins at the level of the nerve endings and ends in a massive loss of myelinized fibres in the motor nerves and especially in the phrenic nerve which ensures the inervation of the diaphragm (Schmalbruch 1991). Contrary to the $FALS_{G93A}$ mouse, this muscular denervation is very rapid and is virtually unaccompanied by signs of reinervation by regrowth of axonal collaterals. On the electromyographic level, the process of muscular denervation is characterized by the appearance of fibrillations and by a significant reduction in the amplitude of the muscular response caused after supramaximal electric stimulation of the nerve (Kennel et al. 1996).

A line of Xt/pmn transgenic mice has also been used as another murine model of ALS. These mice were obtained by a first crossing between C57/B156 or DBA2 female mice and Xt pmn$^+$/Xt$^+$pmn male mice (strain 129), followed by a second between descendants Xt pmn$^+$/Xt$^+$pmn$^+$ heterozygous females (N1) with initial males. Among the descendant mice (N2), the Xt pmn$^+$/Xt$^+$pmn double heterozygotes (called "Xt pmn mice") carrying an Xt allele (demonstrated by the Extra digit phenotype) and a pan allele (determined by PCR) were chosen for the future crossings.

2. Expression Systems 2.1. Plasmid Vectors

Various plasmid vectors allowing the expression of one or two neurotrophic factors can be used. It is possible to mention, for example, the pCRII-BDNF and pSh-Ad-BDNF plasmids, which contain an expression and BDNF secretion cassette (WO95/25804). It is likewise possible to mention the p-LTR-IX-GDNF plasmids containing a nucleic acid coding for GDNF under the control of the promoter LTR (WO95/26408) as well as the p-LVR-IX-preNGF/CNTF plasmid containing the sequence of the CNTF gene behind the signal sequence of the betaNGF as well as the inverted repeated sequences (ITR) of the adenoviral genome, the LTR sequences of the promoter of the Rous Sarcoma virus (RSV), encapsidation sequences as well as adenoviral sequences necessary for homologous recombination. It is understood that any plasmid containing a replication origin and a marker gene can be used to construct an expression system according to the invention by insertion of one or more expression cassettes of a neurotrophic factor. The plaids can be prepared in a eucaryotic or procaryotic cell host.

2.2.—Adenovirus

As indicated above, the viral vectors, and especially the adenoviruses, constitute a particularly preferred mode of realization of the invention.

The recombinant adenoviruses used below were obtained by homologous recombination according to the techniques described in the prior art. In brief, they are constructed in 293 cells by recombination between a fragment of linearized viral genome (dl324) and a plasmid containing the left ITR, the encapsidation sequences, the transgene as well as its promoter and viral sequences allowing recombination. The viruses are amplified in 293 cells. They are regularly repurified in the P3 in our laboratory. The viral genomes can likewise be prepared in a procaryotic cell according to the technique described in the Application WO96/25506. The following viruses were more particularly used:

Ad-CNTF: Recombinant adenovirus of Ad5 serotype comprising, inserted in its genome in place of the deleted E1 region, an expression cassette of the CNTF gene composed of the cDNA coding for CNTF under the control of a transcriptional promoter (in particular the LTR of RSV). The details of the construct are given in the Application WO94/08026. Alternative constructs comprise a supplementary deletion in the E4 region, such as described in the Application WO96/22378 or in the E3 region.

AD-GDNF: Recombinant adenovirus of Ad5 serotype comprising, inserted in its genome in place of the deleted E1 region, an expression cassette of the GDNF compound of the cDNA coding for GDNF under the control of a transcriptional promoter (in particular the LTR of RSV). The details of the construct are given in the Application WO95/26408). An alternative construct comprises a supplementary deletion in the E4 region, such as described in the Application WO96/22378.

Ad-NT3: Recombinant adenovirus of Ad5 serotype comprising, inserted in its genome in place of the deleted E1 region, an expression cassette of the NT3 gene composed of the CDNA coding for NT3 under the control of a transcriptional promoter (in particular the LTR of RSV). An alternative construct comprises a supplementary deletion in the E4 region, such as described in the Application WO96/22378.

Ad-BDNF; Recombinant adenovirus of Ad5 serotype comprising, inserted in its genome in place of the deleted E1 region, an expression cassette of the BDNF compound of the cDNA coding for BDNF under the control of a transcriptional promoter (in particular the LTR of RSV). The details of the construct are given in the Application WO95/25804. An alternative construct comprises a supplementary deletion in the E4 region, such as described in the Application WO96/22378.

Ad-FGFa: Recombinant adenovirus of Ad5 serotype comprising, inserted in its genome in place of the deleted E1 region, an expression cassette of the FGFa compund of the cDNA coding for FGFa under the control of a transcriptional promoter (in particular the LTR of RSV). The details of the construct are given in the Application WO95/25803. An alternative construct comprises a supplementary deletion in the E4 region, such as described in the Application WO96/22378.

The functionality of the viruses constructed is verified by infection of fibroblasts in culture. The presence of the corresponding neurotrophic factor is analysed in the culture supernatant by ELISA and/or by demonstrating the trophic properties of this supernatant on neuronal primary cultures.

3. Administration of Recombinant Adenovirus

The adenoviruses coding for the neurotrophic factors are administered by the intravenous route in adult or newborn animals. In the adult $FALS_{G93A}$ mice, $10^9$ pfu of each of the adenoviruses (final volume 200 µl) are then injected into the caudal vein with the aid of a Hamilton®-type microsyringe. In the newborn pmn mice (age 2–3 days), identified by the absence of a supernumerary digit, $2 \times 10^9$ pfu (final volume 20 µl) of the adenoviral suspension are injected into the retinal vein with the aid of an insulin-type microsyringe equipped with a 30 g needle. The newborn animals are lightly anaesthetized with ether and in a state of hypothermia.

4. Miscellaneous Techniques

Electromyography

While their physical state allows it, the animals are anesthetized by intraperitoneal injection of a mixture of diazepam (Valium®, Roche, France) and of ketamine hydrochloride (Ketalar®, Parke-Davis, France) at a rate of 2 µg/g and 60 µg/g of body weight respectively.

The electromyograph used is a latest generation apparatus (Keypoint®) having all of the software necessary for the acquisition and for the treatment of electromyographic signals. This material is leased to Dantec (Les Ulis, France).

Electromyography of Stimulo-detection: Motor Response Evoked (REM)

When an electric shock is applied to a nerve, the muscles innervated by this nerve are the site of an electrical response. This survives for a certain time (distal latency) which corresponds to the conduction time of the stimulation as far as the synapses, to which is added the transmission time of the signal in the synapse. The amplitude of the response is proportional to the quantity of innervated muscular fibres.

For purely practical reasons, we have chosen to stimulate the sciatic nerve picking up the motor response evoked at the level of the gastrocnemius muscle of the calf. Five needle electrodes (Dantec) are directly implanted and connected to the electromyograph according to the following scheme: (a) 2 stimulation electrodes are placed, one (active electrode) on the path of the sciatic nerve, the other (reference electrode) at the base of the tail; (b) 2 detection electrodes are implanted, one in the gastrocnemius muscle (active electrode), the other on the corresponding tendon (reference electrode); (c) finally one electrode is connected to earth and is implanted between the two active electrodes, in the thigh of the animal. The amplitude and the latency of the REM of the muscle are measured with a stimulation of its motor nerve. This lasts 200 ms at a supramaximal intensity which corresponds to 150% of the intensity allowing the maximum action potential to be obtained. In the adult mouse, if the muscle and the nerve studied are sound, and under the conditions described above, the amplitude of the response evoked is more than or equal to 80 mV, and the latency time is in general equal to 0.6 ms.

Histological Analysis

The animals are killed by chloroform overdose and perfused intracardially with a solution of glutaraldehyde. The phrenic nerves are isolated, removed, subsequently fixed with osmium tetroxide and included in epoxy. The phrenic nerves are cut close to the diaphragm, and sections of a thickness of 3 μm are stained with paraphenyldiamine and analysed by optical microscopy.

5.—Administration of an Expression System Expressing the CNTF Gene

Injection of Adenoviral Vector:

$Xt^+pmn/Xt^+pmn$ homozygous mice ("pmn mice") aged 2 to 3 days, identified by the absence of a supernumerary digit, were used for the injection of adenoviral vector. A suspension of adenoviral CNTF was prepared by dilution of the adenoviral stock in a salinephosphate buffer (PBS) at $2\times10^9$ pfu/μl and administered according to the conditions described in item 3. The AdlacZ coding in *E. coli* for β-galacto-sidase (Stratford-Perricaudet, 1992) was used as a control adenoviral vector.

Results:

Analyses by Northern blot of human fibroblasts infected with AdCNTF demonstrate the presence of two recombinant transcripts of a respective size of 1.1 and 1.6 kb. The analyses by ELISA reveal the presence of recombinant proteins in the supernatants after infection of different types of cells.

All the non-treated pmn mice in the experimental series are dead before the age of two months and the average of their survival was 40.4±2.4 days (n=14). The administration of the AdlacZ control vector did not modify the survival of the pmn mice. On the contrary, the pmn mice treated with intravenous injections of AdCNTF survived up to 73 days (FIG. 3). The average of the survival of the pmn mice treated with AdCNTF was significantly improved and represents 52.7±3.9 days (n=7, p<0.011) (The differences between the results of the Xt/pmn healthy mice, nontreated homozygous vice and treated pmn mice were analysed by the Student's t test. The values are given as mean±standard error of the mean (SEM)).

In order to determine whether the prolongation of the survival of the pmn mice treated with AdCNTF reflected an increase in the number of phrenic nerve fibres, optical microscopy on day 25 was carried out and showed that in the non-treated pmn mice and in the pmn mice who had received AdlacZ intravenously the number of myelinized fibres in the phrenic nerves had decreased respectively to 122±13 (n=6) and 111±11 (n=8) compared with 263±8 myelinized fibres in healthy mice (n=4). The number of myelinized fibres in the phrenic nerves of pmn mice who were injected with AdCNTF was significantly greater than that of the control animals (145±11, n=10, p<0.05). Thus treatment of the pmn mice with ADCNTF induces a reduction of 20% in the loss of myelinized fibres (FIG. 4).

6. Administration of an Expression System Producing a CNTF-GDNF Combination $10^9$ pfu of each of the Ad-CNTF and Ad-GDNF adenoviruses were injected (caudal vein) with the aid of a microsyringe in a final volume of 200 μl into 4 $FALS_{G93A}$ mice aged 99 days. In the course of time, the electromyographic performances of the animals were followed and compared with a control group. The average duration of life was likewise recorded.

Electromyography

The results obtained are presented in FIG. 1. A lowering of the amplitude of the motor response evoked (REM) is observed in the gastrocnemius of the treated $FALS_{G93A}$ mice (AdCNTF+AdGDNF) as well as non-treated $FALS_{G93A}$ mice. This lowering reflects the progressive denervation process which is a characteristic of ALS. Nevertheless, the treated mice show an REM amplitude which is systematically higher than that of the controls, demonstrating a slowing of the functional attack following treatment.

Longevity

The duration of life of the animals is indicated in the tables below.

Treated Animals

| Animal No. | Age at death |
| --- | --- |
| 1779-5 | 188 |
| 1779-6 | 170 |
| 1779-7 | 176 |
| 1779-8 | 155 |
| Average | 172.2 |
| SEM | 6.86 |

Non-treated Animals

| Animal No. | Age at death |
| --- | --- |
| 35-5 | 142 |
| 35-8 | 135 |
| 35-9 | 151 |
| 35-50 | 125 |
| 35-60 | 147 |

-continued

| Animal No. | Age at death |
|---|---|
| 35-90 | 155 |
| Average | 142.5 |
| SEM | 4.51 |

The results show that all the animals of the treated group are dead at an age which is higher than or equal to the age of the oldest living animal in the control group. These results likewise show an increase in the duration of life in the treated animals of 30 days on average, with respect to the control animals. These results are particularly unexpected and, compared to 13 days obtained with Rilutek[R], demonstrate the therapeutic potential of the method of the invention.

7. Administration of an Expression System Producing NT3

7(a)—Administration of an Expression System Producing NT3 (Mice Aged 99 Days)

$10^9$ pfu of Ad-NT3 adenovirus were injected (caudal vein) with the aid of a microsyringe in a final volume of 200 µl into 4 FALS$_{G93A}$ mice aged 99 days. In the course of time, the electromyographic performances of the animals are followed and compared to a control group. The results obtained are presented in FIG. 2 and show that the treated animals show an REM amplitude higher than that of the controls, demonstrating a slowing of the functional attack following treatment.

7(b)—Administration of an Expression System Producing NT3 (Mice Aged 3 Days)

$5.10^9$ pfu of Ad-NT3 adenovirus were injected (temporal vein) with the aid of a microsyringe in a final volume of 20 µl into FALS$_{G93A}$ mice aged 3 days.

The length of life of the animals is indicated in the table below.

Treated Animals

| Animal No. | Age at death |
|---|---|
| 73-1 | 161 |
| 73-2 | 173 |
| 73-3 | 178 |
| 73-4 | 184 |
| 73-5 | 186 |
| 73-6 | 187 |
| 73-7 | 187 |
| 73-8 | 191 |
| 73-9 | 196 |
| 73-10 | 197 |
| 74-1 | 162 |
| 74-2 | 177 |
| 74-3 | 177 |
| 74-4 | 179 |
| 74-5 | 180 |
| 74-6 | 183 |
| 74-7 | 186 |
| 37-1 | 162 |
| 37-2 | 176 |
| 37-3 | 181 |
| 37-4 | 189 |
| 37-5 | 190 |
| 37-6 | 190 |
| Mean | 181.4 |
| SEM | 2.1 |

Non-treated Animals

| Animal No. | Age at death |
|---|---|
| 1-1 | 130 |
| 1-2 | 150 |
| 1-3 | 158 |
| 1-4 | 156 |
| 1-5 | 162 |
| 1-6 | 142 |
| 1-7 | 170 |
| 39-1 | 157 |
| 39-2 | 157 |
| 39-3 | 164 |
| 39-4 | 147 |
| 39-5 | 161 |
| 43-1 | 150 |
| 43-2 | 168 |
| 43-3 | 170 |
| 43-4 | 193 |
| 43-5 | 147 |
| 43-6 | 161 |
| 43-7 | 191 |
| 45-1 | 154 |
| 45-2 | 174 |
| 45-3 | 179 |
| 45-4 | 176 |
| 45-5 | 157 |
| 45-6 | 188 |
| 45-7 | 178 |
| 45-8 | 182 |
| 59-1 | 150 |
| 59-2 | 186 |
| 59-3 | 171 |
| 59-4 | 172 |
| 34-1 | 172 |
| 34-2 | 189 |
| 34-3 | 170 |
| 34-4 | 191 |
| 34-5 | 195 |
| 34-6 | 174 |
| 34-7 | 147 |
| 34-8 | 150 |
| 34-9 | 151 |
| 34-10 | 165 |
| 34-11 | 165 |
| 34-12 | 155 |
| 34-13 | 146 |
| Mean | 165.3 |
| SEM | 2.3 |

The results show an increase of 16.1 days in the average length of life between the animals who have been treated with Ad-NT3 by the intravenous route and the non-treated animals.

8. Administration of an Expression System Producing a CNTF-NT3 Combination $10^9$ pfu of each of the Ad-CNTF and Ad-NT3 adenoviruses were injected (caudal vein) with the aid of a microsyringe in a final volume of 200 µl into 4 animals aged 99 days. In the course of time, the electromyographic performances of the animals were followed and compared with a control group. The average duration of life is likewise recorded.

9. Administration of an Expression System Producing a BDNF-NT3 Combination $10^9$ pfu of each of the Ad-BDNF and Ad-NT3 adenoviruses were injected (caudal vein) with the aid of a microsyringe in a final volume of 200 µl into 4 animals aged 99 days. In the course of time, the electromyographic performances of the animals were followed and compared with a control group. The average duration of life is likewise recorded.

10. Administration of an Expression System Producing BDNF $10^9$ pfu of Ad-BDNF adenovirus were injected (caudal vein) with the aid of a microsyringe in a final volume of 200

µl into 4 animals aged 99 days. In the course of time, the electromyographic performances of the animals are followed and compared with a control group. The average duration of life is likewise recorded.

References

AKLI S. et al. Nature genet., 3,224–228,1993

APPEL S. H. et al. Autoimmunity as an etiological factor in sporadic amyotrophic lateral sclerosis. In Serratrice G. T. and Munsat T. L. eds. *Pathogenesis and therapy of amyotrophic lateral sclerosis.* Advances in Neurology, 68, pp. 47–58, 1995. Lippincott-Raven publishers, Philadelphia.

BAJOCCHI G. et al. Nature genet., 3,229–234, 1993.

BARKATS M. et al. Neuroreport, 7,497–501, 1996.

BARINAGA M. Science 264, 772–774 1994.

CASTEL BARTHE M. N. et al. Neurobiology of Disease, 3, 76–86, 1996.

CHIU A. Y., et al. Mol. Cell. Neurosci., 6, 349–362, 1995.

DAVIDSON B. L., et al. Nature genet., 3, 219–223, 1993.

DITTRICH F. Ann. Neurol., 35, 151–163, 1994.

FINIELS F. et al. Neuroreport, 7,373–378, 1995.

GASTAUT J. L. The viral hypothesis. In Serratrice G. T. and Munsat T. L. eds. *Pathogenesis and therapy of amyotrophic lateral sclerosis.* Advances in Neurology, 68,.pp. 135–138, 1995. Lippincott-Raven publishers, Philadelphia.

GURNEY M. E., PU H., CHIU A. Y. et al. Science, 264, 1772–1775, 1994.

GURNEY M. E., CUTTING F. B., ZHAI P. et al. Ann. Neurol., 39, 147–157, 1996.

HENDERSON C. E., CAMU W., NETTLING C. at al. Nature, 363, 266–270, 1993.

HENDERSON C. E. et al. Science, 266, 1062–1064, 1994.

HENDERSON C. E. Neurotrophic factors as therapeutic agents in amyotrophic lateral sclerosis: potential and pitfalls. In Serratrice G. T. and Munsat T. L. eds. *Pathogenesis and therapy of amyotrophic lateral sclerosis.* Advances in Neurology, 68, pp. 235–240, 1995. Lippincott-Raven publishers, Philadelphia.

HORELLOU P., VIGNE E., CASTEL M. N. et al. Neuroreport, 6, 49–53, 1994.

HUGHES R. A. et al. Neuron, 10, 369–377, 1993.

KENNEL P. F., FINIELS F., REVAH F. et al. Neuroreport, 7, 1427–1431, 1996a.

KENNEL P. F. et al. Neurobiol Disease, 3: 137–147, 1996.

Le GAL La SALLE G. et al. Science, 262, 430–433, 1993.

LEWIS M. E. et al. Exp. Neurol., 124, 73–88, 1993.

OPPENHEIM R. W., YIN Q. W., PREVETTE D. et al. Nature, 360, 755–757, 1992.

OPPENHEIM R. W. et al. Nature, 373, 344–346, 1995.

PENNICA D., ARCE V., SWANSON T. A. et al. Neuron, 17, 63–74, 1996.

PRICE D. L. et al. Neurobiol. Disease, 1, 3–11, 1994.

ROSEN D. R., SIDDIQUE T., PATTERSON D. et al. Nature, 362, 59–62, 1993.

ROTHSTEIN J. D. Excitotoxic mechanisms in the pathogenesis of amyotrophic lateral sclerosis. In Serratrice G. T. and Munsat T. L. eds. *Pathogenesis and therapy of amyotrophic lateral sclerosis.* Advances in Neurology, 68, pp. 7–20, 1995. Lippincott Raven publishers, Philadelphia.

ROWLAND L. P. Proc. Natl. Aca. Sci. USA, 92, 1251–1253, 1995.

RUBIN B. A. and RORKE L. B. Adenovirus vaccines. In Plotkin and Mortimer eds, Vaccines, pp. 492–512, 1988. W. B. Saunders, Philadelphia.

SCHMALBRUCH H., JENSEN H. S., BJAERG M., KAMIENIECKA Z. and KURLAN L. J. Neuropathol Exp Neurol. 50: 192–204, 1991.

SENDTNER K. et al. Nature, 358, 502–504, 1992a.

SENDTNER M., HOLTMANN B., KOLBECK R. Nature, 360, 757–759, 1992b.

SILLEVIS SMITT P. A. E. et al. J. Neurol. Sci., 91, 231–258, 1989.

STRATFORD-PERRICAUDET L. D., MAXEX I., PERRICAUDET M., BRIAND P. J. Clin. Invest. 90, 626–630, 1992.

VEJSADA R., SAGOT Y. and KATO A. C. Eur. J. Neurosci., 7, 108–115, 1995.

WINDEBANK A. J. Use of growth factors in the treatment of motor neuron diseases. In Serratrice G. T. and Munsat T. L. eds. *Pathogenesis and therapy of amyotrophic lateral sclerosis.* Advances in Neurology, 68, pp. 229–234, 1995. Lippincott-Raven publishers, Philadelphia.

YAN Q., ELLIOTT J. and SNIDER W. D. Nature, 360, 753–755, 1992.

YANG Y., ERTL H. C. J., and WILSON J. M. Immunity, 1, 433–442, 1994.

YAN Q., MATHESON C., LOPEX O. T. et al. J. Neurosci., 14, 5281–5291, 1994.

YASE Y. Metal metabolism in motor neuron disease. In Chen K. M. and Yase Y. eds. *Amyotrophic lateral sclerosis in Asia and Oceania,* Taipei, pp. 337–356, 1984. Taiwan: National Taiwan University Press.

YEH P., DEDIEU J. F., ORSINI C. et al. J. Virol., 70, 559–565, 1996.

YIM M. B., et al. Proc. Natl. Acad. Sci. USA, 93, 5709–5714, 1996.

What is claimed is:

1. A pharmaceutical composition comprising two adenovirus vectors, wherein each vector comprises a nucleic acid encoding a different neurotrophic factor.

2. The pharmaceutical composition according to claim 1, wherein the vectors comprise an expression cassette having the coding sequences of two different neurotrophic factors and having sequences that provide for the simultaneous expression of the two different neurotrophic factors.

3. The pharmaceutical composition according to claim 1, wherein the neurotrophic factors are selected from GDNF, BDNF, CNTF and NT3.

4. The pharmaceutical composition according to claim 3, wherein the adenovirus vectors are two replication defective recombinant adenovirus vectors, and wherein one adenovirus vector comprises a nucleic acid encoding CNTF and one adenovirus vector comprises a nucleic acid encoding GDNF.

5. The pharmaceutical composition according to claim 3, wherein the adenovirus vectors are two replication defective recombinant adenoviruses adenovirus vectors and wherein one adenovirus vector comprises a nucleic acid encoding GDNF and one adenovirus vector comprises a nucleic acid encoding NT3.

6. The pharmaceutical composition according to claim 3, wherein the adenovirus vectors are two replication defective recombinant adenovrus vectors, and wherein one adenovirus vector comprises a nucleic acid encoding BDNF and one adenovirus vector comprises a nucleic acid encoding NT3.

7. The pharmaceutical composition according to claim 1, in an injectable form.

8. The pharmaceutical composition according to claim 1, further comprising riluzole.

9. The pharmaceutical composition according to claim 8, in an injectable form.

10. The pharmaceutical composition according to claim 1, wherein one of the neurotrophic factors is CNTF.

11. The pharmaceutical composition of claim 1, wherein one of the neurotrophic factors is BDNF.

12. The pharmaceutical composition of claim 1, wherein at least one adenovirus vector is a replication defective recombinant adenovirus vector.

13. A method of treating amyotrophic lateral sclerosis comprising administering to a subject by systemic administration a pharmaceutical composition comprising an adenovirus vector comprising a nucleic acid encoding a neurotrophic factor, wherein the treatment results in a reduction in progressive motor neuron degeneration in said subject.

14. A method of treating amyotrophic lateral sclerosis comprising administering to a subject by systemic administration a pharmaceutical composition comprising an adenovirus vector comprising a nucleic acid encoding a neurotrophic factor, wherein the treatment results in a reduction in progressive denervation in said subject.

15. The method of claim 13, wherein the reduction in progressive motor neuron degeneration is detectable by a change in the rate of loss of the number of myelinized fibers in a peripheral nervous tissue.

16. The method of claim 14, wherein the reduction in progressive denervation is detectable by electromyography.

17. The method of claim 13, wherein the adenovirus vector comprises an expression a cassette comprising a nucleic acid encoding a neurotrophic factor under the control of a transcriptional promoter.

18. The method of claim 14, wherein the adenovirus vector comprises an expression cassette comprising a nucleic acid encoding a neurotrophic factor under the control of a transcriptional promoter.

19. The method of claim 15, wherein the adenovirus vector comprises an expression cassette comprising a nucleic acid encoding a neurotrophic factor under the control of a transcriptional promoter.

20. The method of claim 16, wherein the adenovirus vector comprises an expression cassette comprising a nucleic acid encoding a neurotrophic factor under the control of a transcriptional promoter.

21. The method of claim 13, wherein the adenovirus vector comprises two expression cassettes, wherein each cassette comprises a nucleic acid encoding a different neurotrophic factor under the control of a transcriptional promoter.

22. The method of claim 14, wherein the adenovirus vector comprises two expression cassettes, wherein each cassette comprises a nucleic acid encoding a different neurotrophic factor under the control of a transcriptional promoter.

23. The method of claim 15, wherein the adenovirus vector comprises two expression cassettes, wherein each cassette comprises a nucleic acid encoding a different neurotrophic factor under the control of a transcriptional promoter.

24. The method of claim 16, wherein the adenovirus vector comprises two expression cassettes, wherein each cassette comprises a nucleic acid encoding a different neurotrophic factor under the control of transcriptional promoter.

25. The method of claim 13, wherein the neurotrophic factor is GDNF, CNTF, BDNF or NT3.

26. The method of claim 14, wherein the neurotrophic factor is GDNF, CNTF, BDNF or NT3.

27. The method of claim 15, wherein the neurotrophic factor is GDNF, CNTF, BDNF or NT3.

28. The method of claim 16, wherein the neurotrophic factor is GDNF, CNTF, BDNF or NT3.

29. The method of claim 13, wherein the adenovirus vector comprises an a bicistronic expression cassette comprising two nucleic acid sequences, wherein each nucleic acid sequence encodes a different neurotrophic factor.

30. The method of claim 29, wherein the neurotrophic factors are selected from GDNF, CNTF, BDNF and NT3.

31. The method of claim 30, wherein the neurotrophic factors are CNTF and GDNF.

32. The method of claim 29, wherein the bicistronic expression cassette further comprises a transcriptional promoter, the promoter selected from a constitutive eucaryotic promoter or a viral promoter.

33. The method of claim 32, wherein the promoter is selected from a CMV, RSV, or adenovirus promoter.

34. The method of claim 13, wherein the systemic administration comprises intravenous administration.

35. The method of claim 14, wherein the systemic administration comprises intravenous administration.

36. The method of claim 15, wherein the systemic administration comprises intravenous administration.

37. The method of claim 16, wherein the systemic administration comprises intravenous administration.

38. The method of claim 13, further comprising administering riluzole.

39. The method of claim 14, further comprising administering riluzole.

40. The method of claim 15, further comprising administering riluzole.

41. The method of claim 16, further comprising administering riluzole.

42. The method of claim 21, further comprising administering riluzole.

43. The method of claim 22, further comprising administering riluzole.

44. The method of claim 25, further comprising administering riluzole.

45. The method of claim 26, further comprising administering riluzole.

46. A method of treating amyotrophic lateral sclerosis comprising administering to a subject by systemic administration a pharmaceutical composition comprising an adenovirus vector comprising a nucleic acid encoding a neurotrophic factor, wherein the treatment results in increased lifespan for said subject.

47. The method of claim 46, wherein the adenovirus vector comprises an expression cassette comprising a nucleic acid encoding a neurotrophic factor under the control of a transcriptional promoter.

48. The method claim 46, wherein the adenovirus vector comprises two expression cassettes, wherein each cassette comprises a nucleic acid encoding a different neurotrophic factor under the control of a transcriptional promoter.

49. The method of claim 46, wherein the neurotrophic factors is one of GDNF, CNTF, BDNF or NT3.

50. The method of claim 46, wherein the adenovirus vector comprises a bicistronic expression cassette comprising two nucleic acid sequences, wherein each nucleic acid sequence encodes a different neurotrophic factor under the.

51. The method of claim 48, wherein the neurotrophic factors are selected from GDNF, CNTF, BDNF and NT3.

52. The method of claim 48, wherein the neurotrophic factors are CNTF and GDNF.

53. The method of claim 47, wherein the transcriptional promoter is a constitutive eucaryotic or viral promoter.

54. The method of claim 53, wherein the promoter is selected from a CMV, RSV, or adenovirus promoter.

55. The method of claim 46, wherein the neurotrophic factors is CNTF.

56. The method of claim 46, wherein the neurotrophic factors is GDNF.

57. The method of claim 46, wherein the neurotrophic factors is BDTF.

58. The method of claim 46, wherein the neurotrophic factors is NT3.

59. The method of claim 46, further comprising administering riluzole.

60. The method of claim 48, further comprising administering riluzole.

61. The method of claim 49, further comprising administering riluzole.

62. The method of claim 46, wherein the systemic administration comprises intravenous administration.

63. The method of claim 48, wherein the systemic administration comprises intravenous administration.

64. The method of claim 49, wherein the systemic administration comprises intravenous administration.

65. The method of claim 59, wherein the systemic administration comprises intravenous administration.

* * * * *

UNITED STATES PATENT AND TRADEMARK OFFICE
CERTIFICATE OF CORRECTION

PATENT NO. : 6,723,315 B1
DATED : April 20, 2004
INVENTOR(S) : Jacques Mallet et al.

It is certified that error appears in the above-identified patent and that said Letters Patent is hereby corrected as shown below:

Column 18,
Line 53, change "adenoviruses adenovirus" to -- adenovirus --.

Column 19,
Line 1, change "according to" to -- of --.
Line 27, change "a cassette" to -- cassette --.
Line 60, change "of transcriptional" to --transcriptional --.

Column 20,
Line 4, change "comprises an a" to -- comprises a --.
Line 55, change "factors" to -- factor --.
Line 59, change "factor under the" to -- factor. --.

Column 21,
Lines 2, 4, 6 and 8, "factors" to -- factor --.

Signed and Sealed this

Twenty-third Day of November, 2004

JON W. DUDAS
*Director of the United States Patent and Trademark Office*